United States Patent
Drew et al.

(10) Patent No.: US 12,138,418 B2
(45) Date of Patent: Nov. 12, 2024

(54) FLUID DRUG SPREAD-PROMOTING PUMP

(71) Applicant: Medtronic, Inc., Minneapolis, MN (US)

(72) Inventors: Touby A. Drew, Eden Prairie, MN (US); Jeffrey P. Bodner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 20 days.

(21) Appl. No.: 17/938,224

(22) Filed: Oct. 5, 2022

(65) Prior Publication Data

US 2023/0158225 A1 May 25, 2023

Related U.S. Application Data (60) Provisional application No. 63/283,126, filed on Nov. 24, 2021.

(51) Int. Cl.
*A61M 5/14* (2006.01)

(52) U.S. Cl.
CPC ....... *A61M 5/14* (2013.01); *A61M 2205/3523* (2013.01); *A61M 2205/50* (2013.01)

(58) Field of Classification Search
CPC ............ A61M 5/14; A61M 2205/3523; A61M 2205/50
See application file for complete search history.

(56) References Cited

U.S. PATENT DOCUMENTS

| | | | | |
|---|---|---|---|---|
| 4,699,615 A | * | 10/1987 | Fischell | A61M 5/1424 604/153 |
| 4,813,951 A | | 3/1989 | Cannon | |
| 5,011,472 A | * | 4/1991 | Aebischer | A61M 5/14276 604/153 |
| 6,349,740 B1 | * | 2/2002 | Cho | A61M 5/365 204/601 |
| 7,559,926 B1 | | 7/2009 | Blischak | |
| 10,953,151 B2 | | 3/2021 | Lin | |
| 2004/0199128 A1 | * | 10/2004 | Morris | A61M 5/14276 604/284 |
| 2005/0277912 A1 | * | 12/2005 | John | A61M 5/16827 604/890.1 |
| 2010/0049127 A1 | * | 2/2010 | Haueter | A61M 5/16881 604/246 |
| 2021/0077714 A1 | | 3/2021 | Bodner | |

FOREIGN PATENT DOCUMENTS

FR  2654937 A * 5/1991  ..........  A61M 27/002

* cited by examiner

*Primary Examiner* — Philip R Wiest
*Assistant Examiner* — Matthew Wrubleski
(74) *Attorney, Agent, or Firm* — Husch Blackwell LLP (57) ABSTRACT

An implantable infusate spread promoting system configured to enable improved dispersion of delivered infusate. The system including an implantable device configured to enable infusate delivery within a body of a patient, and an implantable manually actuatable flushing pump configured to remove and re-inject a quantity of fluid with each actuation to promote improved dispersion of the delivered infusate.

21 Claims, 7 Drawing Sheets

FLUID DRUG SPREAD-PROMOTING PUMP

CROSS-REFERENCE TO RELATED APPLICATION

This application claims the benefit of and priority to U.S. Provisional Patent Application No. 63/283,126 filed Nov. 24, 2021, the entire disclosure of which is incorporated by reference herein.

TECHNICAL FIELD

The present technology is generally related to implantable medical devices, and more particularly to a fluid drug spread promoting device enabling enhanced mixing of an infused drug via a manually activated flushing pump.

BACKGROUND

Implantable medical devices, such as implantable medical pumps and ports, are useful in managing the delivery and dispensation of prescribed therapeutic agents, nutrients, drugs, infusates such as antibiotics, blood clotting agents, analgesics and other fluid or fluid like substances (collectively "infusate" or "infusates") to patients in volume- and time-controlled doses as well as through boluses. Such implantable pumps and ports are particularly useful for treating diseases and disorders that require regular or chronic (i.e., long-term) pharmacological intervention, including tremor, spasticity, multiple sclerosis, Alzheimer's disease, Parkinson's disease, amyotrophic lateral sclerosis (ALS), Huntington's disease, cancer, epilepsy, chronic pain, urinary or fecal incontinence, sexual dysfunction, obesity, and gastroparesis, to name just a few. Depending upon their specific designs and intended uses, implantable pumps and ports are well adapted to administer infusates to specific areas within the vasculatures and central nervous system, including the subarachnoid, epidural, intrathecal, and intracranial spaces or provide access to those spaces for aspiration.

Providing access to the cerebrospinal fluid for the administration of infusates or aspiration of fluid has a number of important advantages over other forms of infusate administration. For example, oral administration is often not workable because the systematic dose of the substance needed to achieve the therapeutic dose at the target site may be too large for the patient to tolerate without adverse side effects. Also, some substances simply cannot be absorbed in the gut adequately for a therapeutic dose to reach the target site. Moreover, substances that are not lipid soluble may not cross the blood-brain barrier adequately if needed in the brain. In addition, infusion of substances from outside the body requires a transcutaneous catheter or access with a hypodermic needle, which results in other risks such as infection or catheter dislodgment. Further, implantable pumps avoid the problem of patient noncompliance, namely the patient failing to take the prescribed drug or therapy as instructed.

Despite these clear advantages, clinicians report that drug boluses delivered via a hypodermic needle during initial patient trialing can in some cases be more effective than delivery of the same dose via an implantable pump or port. Factors that may account for the more effective delivery include infusion of the bolus at a higher velocity followed by the clinician cycling the syringe plunger to affect barbotage (e.g., the repeated injection and removal of fluid), which may further enhance mixing. The present disclosure addresses this concern.

SUMMARY OF THE DISCLOSURE

The techniques of this disclosure generally relate to an implantable infusate spread promoting device configured to enable enhanced mixing of infusate delivered with an implantable pump or port via manual barbotage. In particular, embodiments of the present disclosure include a manually activated flushing pump (also referred to herein as a "button" or "modular patient compressible reservoir" that is manually depressed or actuated to the skin of the patient, thereby removing and re-injecting a quantity of fluid (e.g., 1 mL of fluid, etc.) with each actuation. Accordingly, multiple actuations of the flushing pump can be used to establish a desired degree of mixing of the infusate with biological fluid at the targeted drug delivery site.

Accordingly, embodiments of the present disclosure enable enhanced mixing of infusate delivered via an implantable pump or port. In some embodiments, the manually activated flushing pump can be incorporated into an implantable pump (e.g., incorporated into a top shield of the pump). Alternatively, the manually activated flushing pump can be separate from the pump or port. For example, in some embodiments, the flushing pump can be positioned in line along the primary drug delivery catheter, such that infusate delivered by the pump or port naturally flows through the manually activated flushing pump. In other embodiments, the flushing pump can be fluidly coupled to the primary drug delivery catheter via a second lumen, such that infusate delivered by the pump or port need not flow through the flushing pump prior to delivery at the targeted drug delivery site.

In embodiments, the manually activated flushing pump can take various forms, such as a molded rubber component, miniature metal bellows, deformable stamped metal cover, or the like. In some embodiments, an implantable pump or port in combination with the flushing pump (collectively referred to herein as a "system") can detect actuation of the flushing pump through pressure sensors or other mechanisms to remind a patient that manual activation may be required if not performed shortly after infuse a delivery. Moreover, in some embodiments, the system can provide prospective reminders to the patient in coordination with infusate delivered.

One embodiment of the present disclosure provides an implantable infusate spread promoting system configured to enable improved dispersion of delivered infusate, including an implantable device configured to enable infusate delivery within a body of a patient, and an implantable manually actuatable flushing pump configured to remove and re-inject a quantity of fluid with each actuation to promote improved dispersion of the delivered infusate.

In one embodiment, the implantable manually actuatable flushing pump is at least one of a molded rubber pushbutton, mechanical bellows, or deformable plate. In one embodiment, the implantable manually actuatable flushing pump comprises a chamber having a volume of between about 0.25 mL and about 2 mL.

In one embodiment, the implantable manually actuatable flushing pump is integrally mounted within a housing of the implantable device. In one embodiment, the implantable manually actuatable flushing pump is fluidly coupled to a catheter extending from the implantable device. In one embodiment, the implantable manually actuatable flushing pump is fluidly coupled in-line with the catheter. In one embodiment, the implantable manually actuatable flushing pump is fluidly coupled to the catheter with a branched coupling. In one embodiment, the implantable manually actuatable flushing pump is configured to draw bodily fluid from an area of a patient spaced apart from a targeted drug delivery site. In one embodiment, the implantable manually actuatable flushing pump is actuatable through skin of a patient. In one embodiment, the implantable manually actuatable flushing pump is passively actuatable through regular patient motion.

In one embodiment, the system further includes a pressure sensor configured to detect manual actuation of the implantable manually actuatable flushing pump. In one embodiment, the pressure sensor is further configured to aid in detection and diagnosis of catheter occlusion, dislodgment, and kink issues. In one embodiment, the system further includes an external programmer in wireless communication with the implantable device. In one embodiment, the external programmer is configured to provide user notifications regarding actuation of the implantable manually actuatable flushing pump. In one embodiment, the implantable device comprises at least one of an implantable pump or implantable port.

Another embodiment of the present disclosure provides an implantable flushing mechanism including an implantable manually actuatable flushing pump in the form of at least one of a rubber pushbutton, mechanical bellows, or deformable plate configured to remove and re-inject a quantity of fluid with each actuation to promote improved dispersion of infusate delivered by an implantable infusion pump. In one embodiment, the implantable manually actuatable flushing pump comprises a chamber having a volume of between about 0.25 mL and about 2 mL. In one embodiment, the implantable manually actuatable flushing pump is fluidly coupled to a catheter extending from the implantable device. In one embodiment, the implantable manually actuatable flushing pump is actuatable through a skin of a patient.

Yet another embodiment of the present disclosure provides an implantable infusate spread promoting system including an implantable pump configured to enable infusate delivery to a catheter positioned within a body of the patient, and an implantable manually actuatable flushing pump configured to remove and re-inject a quantity of fluid of between about 0.25 mL and about 2 mL with each actuation to promote improved dispersion of the delivered infusate, the implantable manually actuatable flushing pump fluidly coupled to the catheter of the implantable pump.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Figure 1:
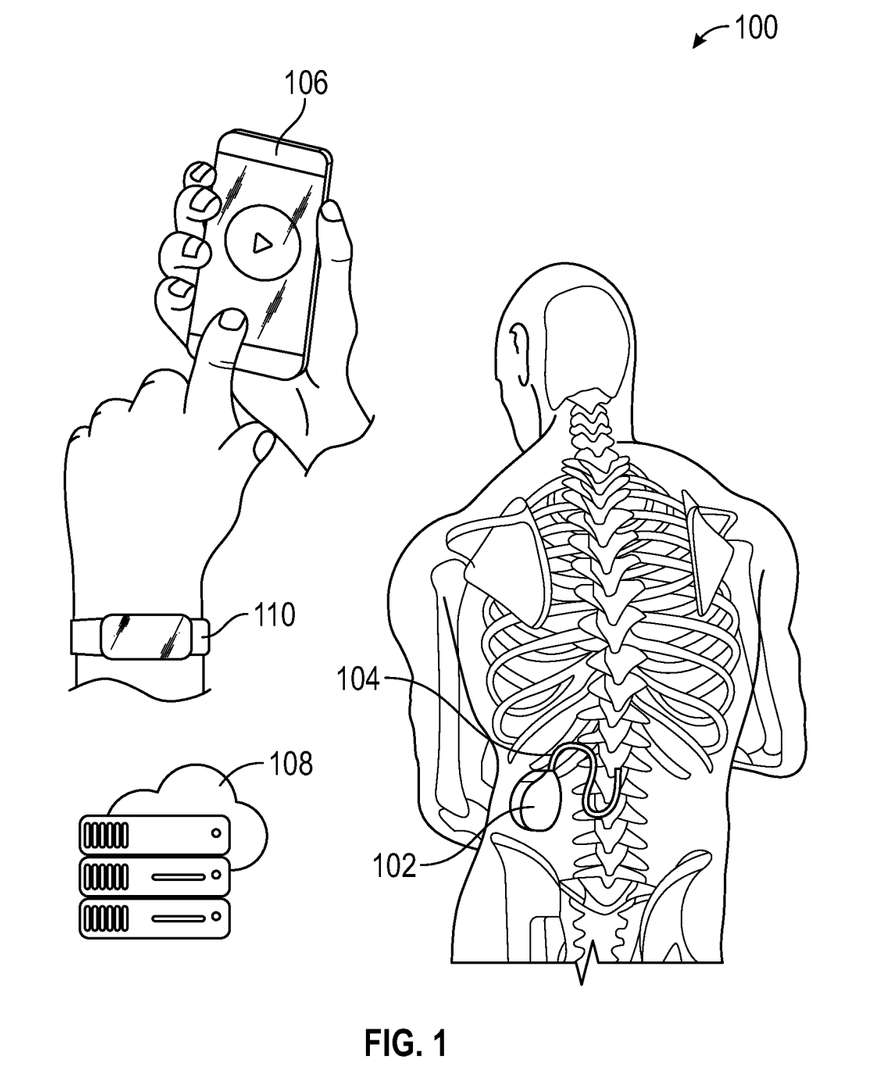
FIG. 1 is a schematic view depicting a medical system configured to enable enhanced mixing of infusate delivered with an implantable pump or port via manual barbotage, in accordance with an embodiment of the disclosure.

Referring to FIG. 1, a medical system 100 comprising an implantable medical device 102 configured to enable enhanced mixing of infusate delivered with an implantable pump or port via manual barbotage, is depicted in accordance with an embodiment of the disclosure. In embodiments, the medical system 100 can include an implantable catheter 104, which can be in fluid communication with the implantable medical device 102, which can be an implantable pump or port, configured to dispense infusate over an extended period of time. As depicted, the implantable device 102 can be implanted within the body of a patient, for example, in an interior torso cavity or in proximity to the patient's ribs or cranially for the introduction of infusate into the patient (e.g., within an intrathecal space, intracranial space, pulmonary artery, etc.) for targeted delivery of infusate. In some embodiments, the implantable device 102 can be placed subcutaneously, and can be held in position by sutures or other retaining features.

Various example embodiments of implantable medical devices, systems and methods are described herein providing enhanced mixing of infusate delivered by an implantable pump or port via a user activated flushing pump. Although specific examples of implantable medical pumps are provided, it is to be appreciated that the concepts disclosed herein are extendable to other types of implantable devices. It is also to be appreciated that the term "clinician" refers to any individual that can prescribe and/or program a therapeutic regimen with any of the example embodiments described herein or alternative combinations thereof. Similarly, the term "patient" or "subject," as used herein, is to be understood to refer to an individual or object in which the infusate delivery is to occur, whether human, animal, or inanimate. Various descriptions are made herein, for the sake of convenience, with respect to the procedures being performed by a clinician on a patient or subject (the involved parties collectively referred to as a "user" or "users") while the disclosure is not limited in this respect.

In some embodiments, the medical system 100 can further include an optional external programmer 106 and optional server 108 configured to communicate with the implantable device 102. In some embodiments, the programmer 106 can be a handheld, wireless portable computing device, such as a cellular telephone, tablet, dedicated implantable device programmer, or the like. Further, in some embodiments, the medical system 100 can include one or more external physiological sensors 110, which can be in communication with the implantable device 102, optional external programmer 106, and optional server 108. In one embodiment, one or more physiological sensors 110 can be incorporated into the implantable device 102 or the external programmer 106. In one embodiment, a physiological sensor 110 can be worn by the patient (e.g., a smart watch, wristband tracker, sensors embedded in clothing, etc.), carried by the patient (e.g., a smart phone, mobile computing device, etc.), or positioned in proximity to the patient (e.g., a stationary monitor, etc.). Examples of physiological sensors 110 include a heart rate monitor, pulse oximeter, respiratory sensor, perspiration sensor, posture orientation sensor, motion sensor, accelerometer, or the like.

Figure 2A:
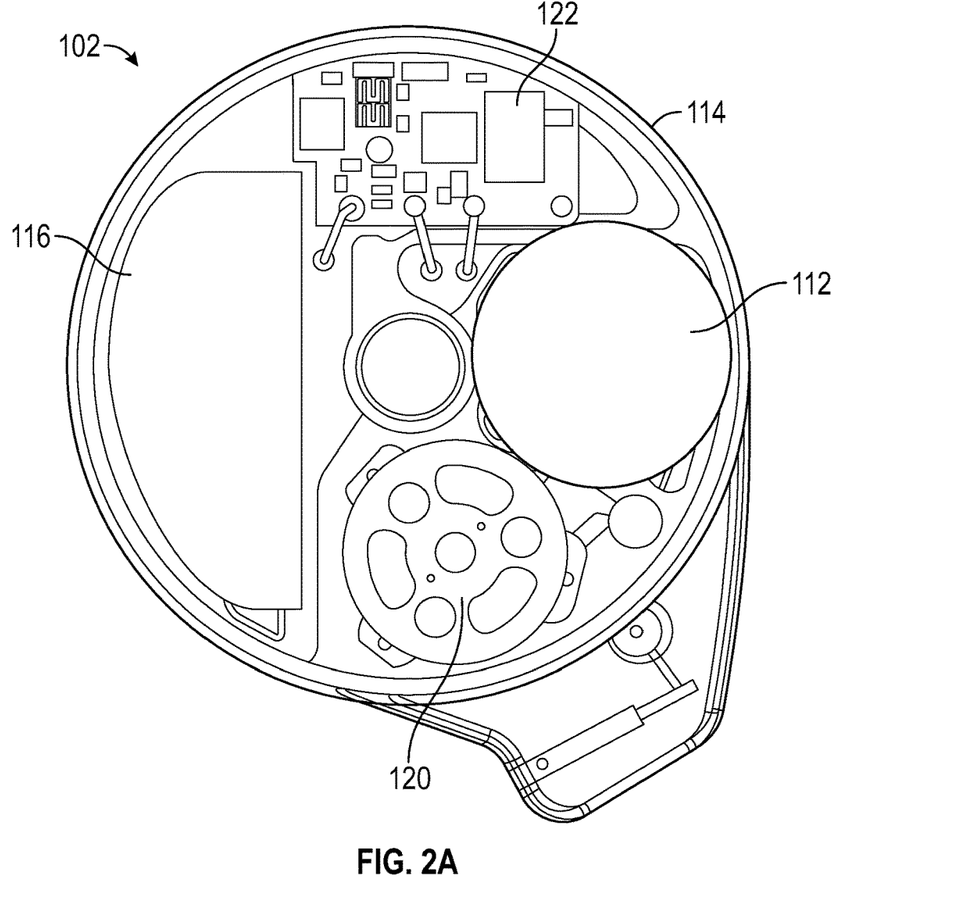
FIGS. 2A-B are cross sectional views depicting an implantable device configured to incorporating a manually activated flushing pump into a housing of the implantable device, in accordance with an embodiment of the disclosure.
Figure 2B:
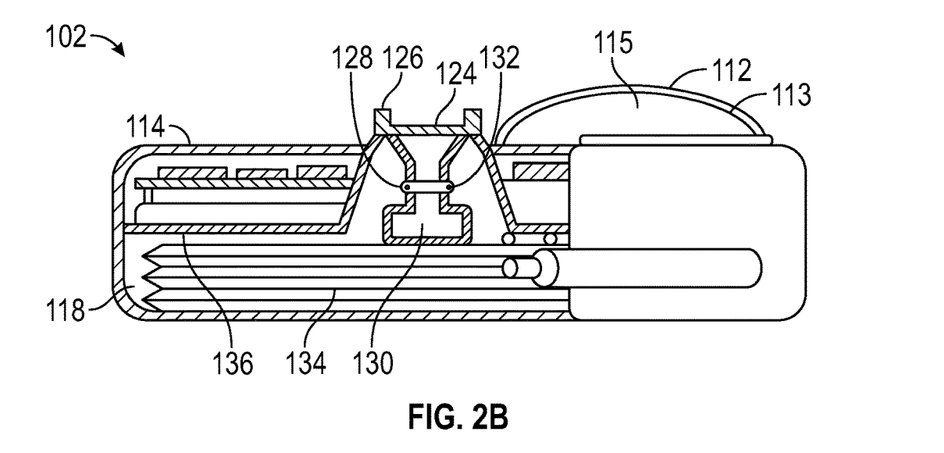

Referring to FIGS. 2A-B, cross sectional views of an implantable pump 102 incorporating a manually activated flushing pump 112 into a housing 114 of the implantable pump 102, are depicted in accordance with an embodiment of the disclosure. The implantable device 102 can generally include a housing 114 (e.g., into a top shield, etc.), power source 116, fluid reservoir 118, pump 120, manually activated flushing pump 112, and computing device 122. The housing 114 can be constructed of a material that is biocompatible and hermetically sealed, such as titanium, tantalum, stainless steel, plastic, ceramic, or the like.

The fluid reservoir 118 can be carried by the housing 114 and can be configured to contain infusate. In one embodiment, infusate within the reservoir 118 can be accessed via an access port 124. Accordingly, the access port 124 can be utilized to refill, aspirate, or exchange fluid within the reservoir 118. In some embodiments, the access port 124 can include one or more positional markers 126, for example in the form of a tactile protrusion, one or more lights or LEDs to illuminate through tissue of the patient, an acoustic device to confirm location of the access port 124, and/or one or more wireless location/orientation sensors to aid in positioning of a refilling device relative to the implantable pump 102.

In some embodiments, the access port 124 can include a septum 128 configured to seal a port chamber 130 relative to an exterior of the housing 112. The septum 128 can be constructed of a silicone rubber or other material having desirable self-sealing and longevity characteristics. The port chamber 130 can be in fluid communication with the reservoir 118. In one embodiment, the access port 124 can further include an optional needle detection sensor 132, for example in the form of a mechanical switch, resonant circuit, ultrasonic transducer, voltmeter, ammeter, ohmmeter, pressure sensor, flow sensor, capacitive probe, acoustic sensor, and/or optical sensor configured to detect and confirm the presence of an injection needle of a refilling apparatus.

The reservoir 118 can include a flexible diaphragm 134. The flexible diaphragm 134, alternatively referred to as a bellows, can be substantially cylindrical in shape and can include one or more convolutions configured to enable the flexible diaphragm 134 to expand and contract between an extended or full position and an empty position. In one embodiment, the flexible diaphragm 134 can divide the reservoir 118 into an infusate chamber containing liquid infusate (within the flexible diaphragm 134), and a vapor chamber 136 (surrounding the flexible diaphragm 134). As the infusate chamber is filled with infusate, the flexible diaphragm 134 extends downwardly (with reference to FIG. 2B) toward a bottom portion of the housing 114 until it has reached a maximum volume or some other desired degree of fullness. Alternatively, as the infusate chamber is aspirated, the flexible diaphragm 134 contracts upwardly toward a top portion of the housing 114 until the infusate chamber reaches a minimum volume. In one embodiment, the flexible diaphragm 134 can have a compression spring rate which tends to naturally bias the flexible diaphragm 134 towards an expanded position.

The pump 120 and manually activated flushing pump 112 can be carried by the housing 114. The pump 120 can be in fluid communication with the reservoir 118 and can be in electrical communication with the computing device 122. The pump 120 can be any pump sufficient for pulling infusate from the reservoir 118 for downstream delivery, such as a peristaltic pump, piston pump, a pump powered by a stepper motor or rotary motor, a pump powered by an AC motor, a pump powered by a DC motor, electrostatic diaphragm, piezoelectric motor, solenoid, shape memory alloy, or the like. Infusate from the pump 120 can flow through the manually activated flushing pump 112, which can be configured for manual activation for repeated cycling of fluid (e.g., expelling fluid from the flushing pump and drawing fluid into the flushing pump or vice versa) downstream of the pump 120. In embodiments, the manually activated flushing pump 112 can be any mechanism configured to enable repeated cycling of fluid, such as a molded rubber component, miniature bellows, deformable cover, or the like.

For example, in one embodiment, the flushing pump 112 can include a deformable wall 113 defining a chamber 115. In embodiments, actuation of the flushing pump 112 can cause the deformable wall 113 to temporarily deform under an external pressure thereby decreasing the volume of the chamber 115. Subsequent release of the external pressure can cause a natural bias or resiliency of the deformable wall 113 to return to its original shape, thereby restoring the initial volume of the chamber 115. In embodiments, the manually activated flushing pump 112 can be configured to displace a quantity of fluid sufficient to enable mixing of the infusate with bodily fluids of the patient (e.g., 0.25 mL, 0.5 mL, 0.75 mL, 1.0 mL, 1.25 mL, 1.5 mL, 1.75 mL, 2.0 mL, etc.). Other fluid quantity displacement volumes are also contemplated.

Figure 3:
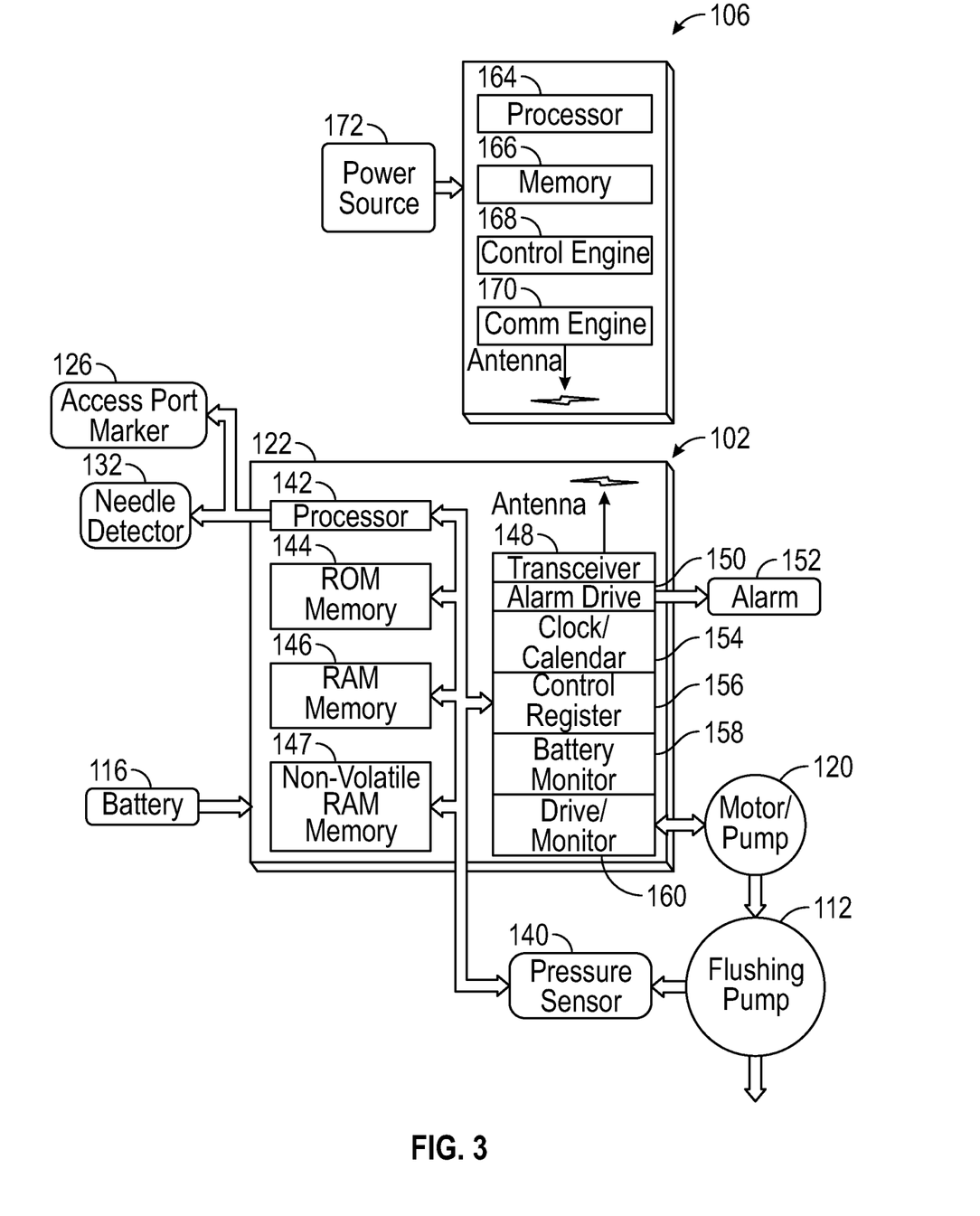
FIG. 3 is a block diagram of an implantable device and programmer configured to enable enhanced mixing of delivered infusate via manual barbotage, in accordance with an embodiment of the disclosure.

Referring to FIG. 3, a block diagram of an implantable pump 102 and programmer 106 configured to enable enhanced mixing of delivered infusate via manual barbotage, is depicted in accordance with an embodiment of the disclosure. The implantable pump 102 can include a computing device 122, which can be carried in the housing 114 (as depicted in FIG. 2A) and can be in electrical communication with the pump 120 and power source 116. The power source 116 can be a battery, such as a rechargeable lithium-ion battery, nickel cadmium battery, or the like. The power source 116, which can be monitored via the battery monitor 158, can be carried in the housing 114 to power the pump 120 and computing device 122. Control of the pump 120 can be directed by a drive/monitor element 160.

The computing device 122 can include a processor 142, memory 144, 146 and 147, and transceiver circuitry 148. In one embodiment, the processor 142 can be a microprocessor, logic circuit, Application-Specific Integrated Circuit (ASIC) state machine, gate array, controller, or the like. The computing device 122 can generally be configured to control delivery of infusate according to programmed parameters or a specified treatment protocol. The programmed parameters or specified treatment protocol can be stored in the memory 144, 146 and 147 for specific implementation by a control register 156. A clock/calendar element 154 can maintain system timing for the computing device 122. In one embodiment, an alarm drive 152 can be configured to activate one or more notification, alert or alarm features, such as an illuminated, auditory or vibratory alarm 152. In some embodiments, the processor 142 can be configured to selectively activate the needle detection sensor 132 and access port marker 126, prior to a physical attempt to insert a needle of the refill device into the access port 124 of the implantable pump 102. Further, in some embodiments, the processor 142 can be configured to receive input from the drive/monitor element 160 and optional pressure sensor 140, which can be configured to monitor for user activation following infusion delivery. Accordingly, in some embodiments, the implantable pump 102 can detect manual actuation of the flushing pump 112 through the pressure sensor 140 to remind the patient then manual activation may be required if not performed shortly after infusion delivery.

Additionally, in some embodiments, the optional pressure sensor 140 can serve as an aid in detecting occlusions and generally monitoring pressure decay within the catheter 104 downstream of the pump 120 to assist in the detection and diagnosis of catheter occlusion, dislodgment, kink in other system 100 issues. Further, in some embodiments, the downstream pressure and pressure decay can be inferred from a sensed electromotive force (EMF) voltage of the pump 120 by noting movement in the rotor of the pump after power has been removed. In operation of the pump 120, drive currents to a stator are selectively applied and removed by the drive/monitor element 160. Through computing device 122, a resulting EMF voltage can be sensed in each of a series of stator coils after the drive currents are removed, from which a position of the rotor can be determined.

In particular, the rotor naturally comes to rest at an equilibrium position determined by the magnetic forces between the stator and rotor, as well as external forces (e.g., pressurized fluid within the catheter 104). In a normal, un-occluded state, the EMF voltage will fluctuate as the rotor rocks back and forth slightly to settle in an equilibrium position. By contrast, when the pump is occluded (and the downstream pressure is elevated), oscillations in the EMF voltage will be diminished, as movement of the rotor is significantly dampened by pressurized medicament trapped downstream. Accordingly, dampened oscillations in sensed EMF voltage can be indicative of slow pressure decay (e.g., occlusion, kinked tubing, system issues, etc.).

The transceiver circuitry 148 can be configured to receive information from and transmit information to the one or more physiological sensors 110, external programmer 106, and server 108. The implantable pump 102 can be configured to receive programmed parameters and other updates from the external programmer 106, which can communicate with the implantable device 102 through well-known techniques such as wireless telemetry, Bluetooth, or one or more proprietary communication schemes (e.g., Tel-M, Tel-C, etc.). In some embodiments, the external programmer 106 can be configured for exclusive communication with one or more implantable devices 102. In other embodiments, the external programmer 106 can be any computing platform, such as a mobile phone, tablet or personal computer. In some embodiments, the implantable device 102 and external programmer 106 can further be in communication with a cloud-based server 108. The server 108 can be configured to receive, store and transmit information, such as program parameters, treatment protocols, drug libraries, and patient information, as well as to receive and store data recorded by the implantable device 102.

In embodiments, various notifications, alerts and alarms regarding timing and instructions for manual barbotage can be presented by the programmer 106. For example, in some embodiments, the programmer 106 can notify a patient that an infusion has occurred or will soon occur, and potentially in combination with pressure sensor 140 can direct the patient to manually actuate the flushing pump 112. In other embodiments, notification can be in the form of vibration or an audible sound from alarm 152. Accordingly, in some embodiments, the system 100 (e.g., via programmer 106 or alarm 152) can provide perspective reminders to the patient in coordination with infusate delivery.

In one embodiment, the programmer 106 or components thereof can comprise or include various modules or engines, each of which is constructed, programmed, configured, or otherwise adapted to autonomously carry out a function or set of functions. The term "engine" as used herein is defined as a real-world device, component, or arrangement of components implemented using hardware, such as by an application specific integrated circuit (ASIC) or field programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations and should generally not be limited to any particular implementation exemplified herein, unless such limitations are expressly called out. In addition, an engine can itself be composed of more than one sub-engine, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

In some embodiments, the programmer 106 can include a processor 164, memory 166, a control engine 168, a communications engine 170, and a power source 172. Processor 164 can include fixed function circuitry and/or programmable processing circuitry. Processor 164 can include any one or more of a microprocessor, a controller, a DSP, an ASIC, an FPGA, or equivalent discrete or analog logic circuitry. In some examples, the processor 162 can include multiple components, such as any combination of one or more microprocessors, one or more controllers, one or more DSPs, one or more ASICs, or one or more FPGAs, as well as other discrete or integrated logic circuitry. The functions attributed to processor 164 herein may be embodied as software, firmware, hardware or any combination thereof.

The memory 166 can include computer-readable instructions that, when executed by processor 164 can direct the control engine 168 to perform various functions. Memory 166 can include volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Control engine 168 can include instructions to control the components of the programmer 106 and instructions to selectively control the implantable medical device 102.

The communications engine 170 can include any suitable hardware, firmware, software, or any combination thereof for communicating with other components of the medical device 102 and/or external devices. Under the control of processor 164, the communication engine 170 can receive downlink telemetry from, as well as send uplink telemetry to one or more external devices (e.g., the implantable medical device 102, etc.) using an internal or external antenna. In addition, communication engine 170 can facilitate communication with a networked computing device and/or a computer network 108. For example, communications engine 170 can receive updates to instructions for control engine 168 from one or more external devices. In another example, communications engine 170 can transmit data regarding the state of system 100 to one or more one or more external devices.

Power source 172 is configured to deliver operating power to the components of the programmer 106. Power source 172 can include a battery and a power generation circuit to produce the operating power. In some examples, the battery is rechargeable to allow extended operation. Power source 172 can include any one or more of a plurality of different battery types. In some embodiments, the programmer 106 can further include an external power supply port.

Figure 4:
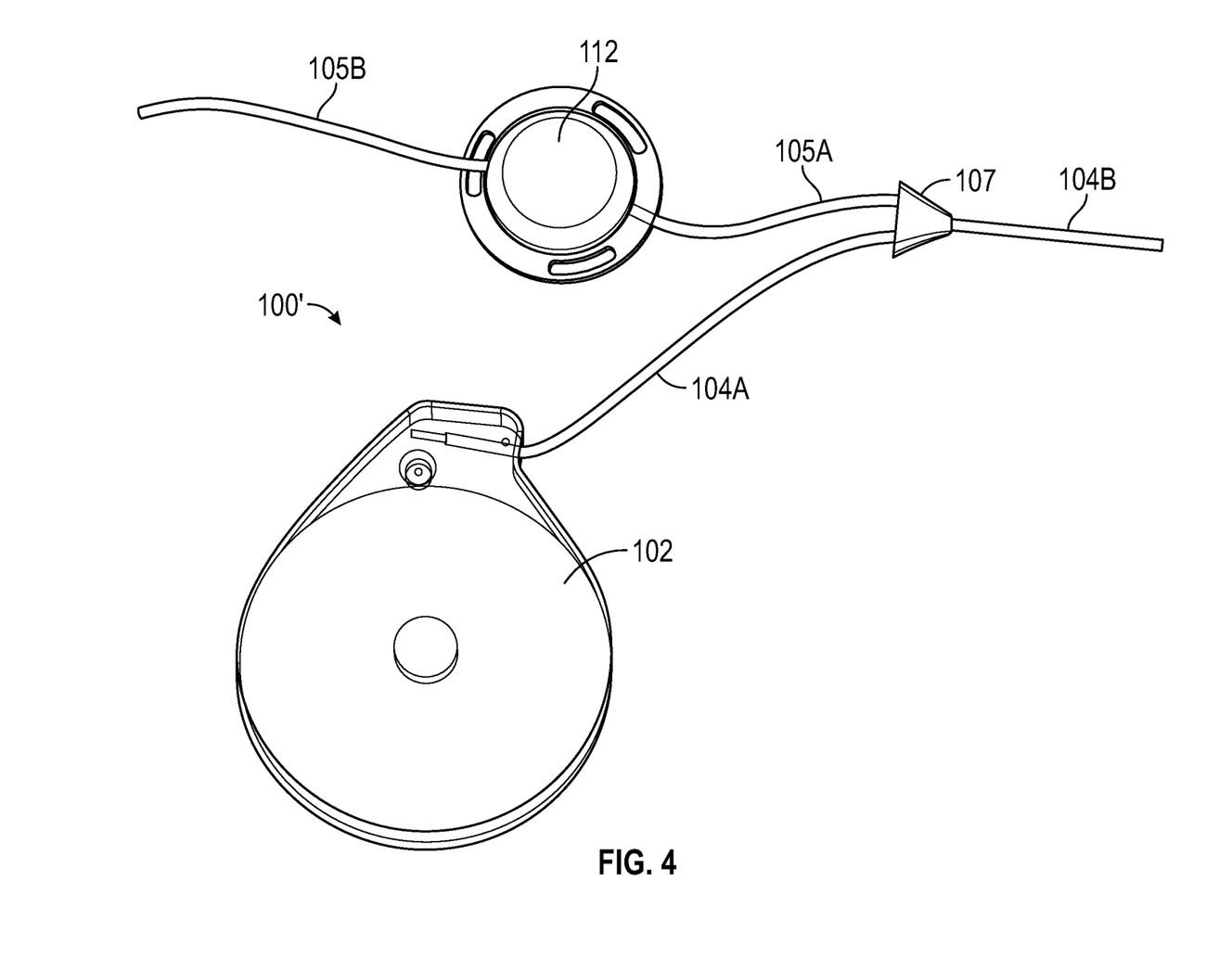
FIG. 4 is a perspective view depicting an implantable infusate spread promoting system configured to enable enhanced mixing of infusate delivered via an implantable pump with manual barbotage via a manually activated flushing pump, in accordance with an embodiment of the disclosure.

With additional reference to FIG. 4, an implantable infusate spread promoting system 100' configured to enable enhanced mixing of infusate delivered via an implantable device 102 with manual barbotage via a manually activated flushing pump 112 is depicted in accordance with an embodiment of the disclosure. Various embodiments of the present disclosure will be described in detail with reference to the drawings, wherein like reference numerals represent like parts and assemblies throughout the several views.

Accordingly, in some embodiments, the flushing pump 112 can be separate from the implantable device 102, such that the manually activated flushing pump 112 is physically separated or distinct from the implantable device 102, thereby enabling the addition of a flushing pump 112 to existing implantable devices 102 to create new systems 100 designed to promote improved mixing of delivered infusates. For example, in some embodiments, the flushing pump 112 can be fluidly coupled in-line with the main catheter 104, such that the flushing pump 112 is positioned between a first catheter portion 104A originating at the implantable device 102, and a second catheter portion 104B terminating at a targeted drug delivery site within the patient (such as that depicted in FIG. 5). In such embodiments, separation of the manually actuated flushing pump 112 from the implantable device 102 enables the flushing pump 112 to be positioned just beneath the patient's skin in an area easily accessible by the user, whereas the implantable device 102 may be positioned deeper within an anterior torso cavity of the patient. Alternatively, separation of the manually actuated flushing pump 112 from the implantable device 102 may enable the flushing pump 112 to be positioned in an area of the patient's body for passive actuation (e.g., via breathing or other natural movement or motion).

In other embodiments (such as that depicted in FIG. 4), the flushing pump 112 can be operably coupled to the main catheter 104 via a secondary lumen 105A, for example via a Y-connector 107 or other branching mechanism. Such embodiments enable the use of a shorter or more direct main catheter 104, for example where the implantable device 102 is positioned relatively close to the target drug delivery site and the flushing pump 112 is positioned some distance away. Moreover, such embodiments may be beneficial in reducing the quantity of medicament potentially retained within the flushing pump 112 between actuations. To further reduce the quantity of medicament pulled into the flushing pump 112, in some embodiments, a tertiary lumen 105B can be fluidly coupled to the flushing pump 112 can be configured to enable fluid to be drawn from one area of the patient (e.g., via tertiary lumen 105B) and expelled through the secondary lumen 105A into the main catheter 104. Other embodiments are also contemplated.

Figure 5:
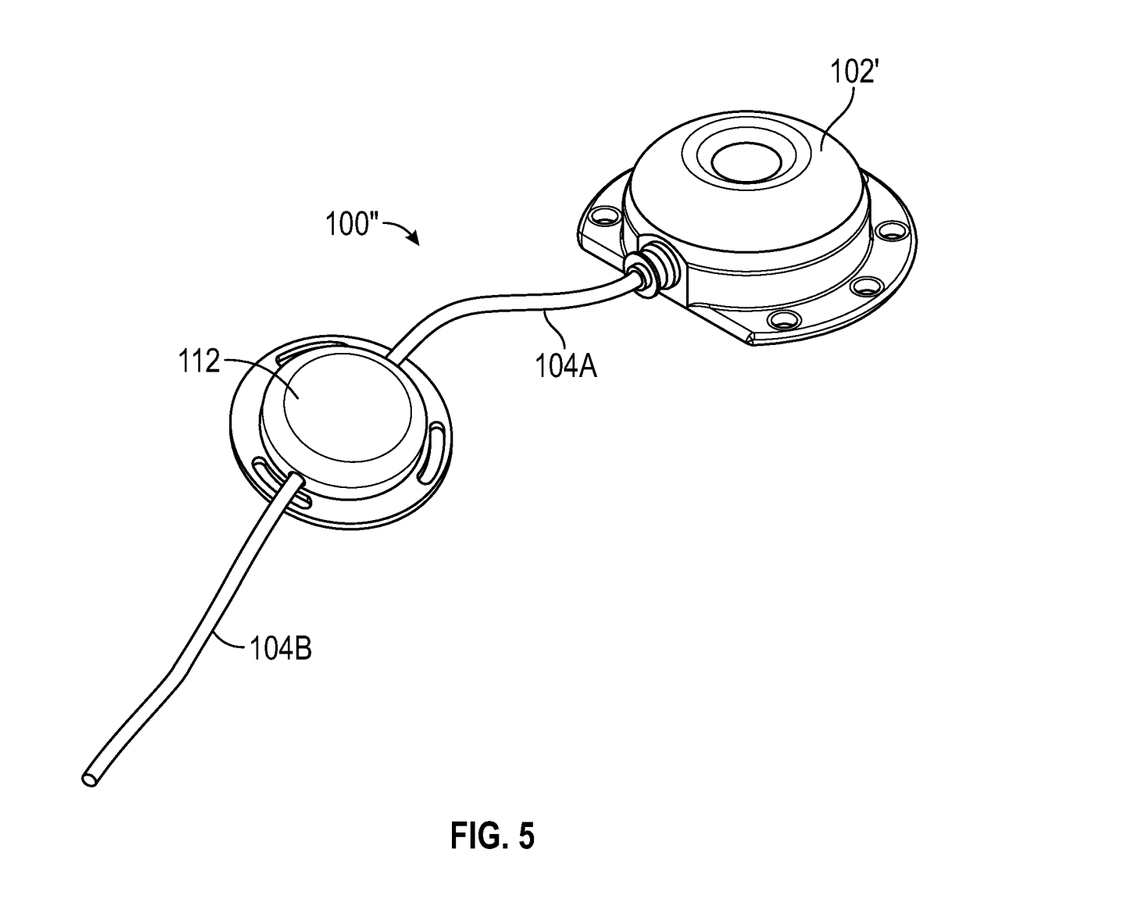
FIG. 5 is a perspective view depicting an implantable infusate spread promoting system configured to enable enhanced mixing of infusate delivered via an implantable port with manual barbotage via a manually activated flushing pump, in accordance with an embodiment of the disclosure.
Figure 6:
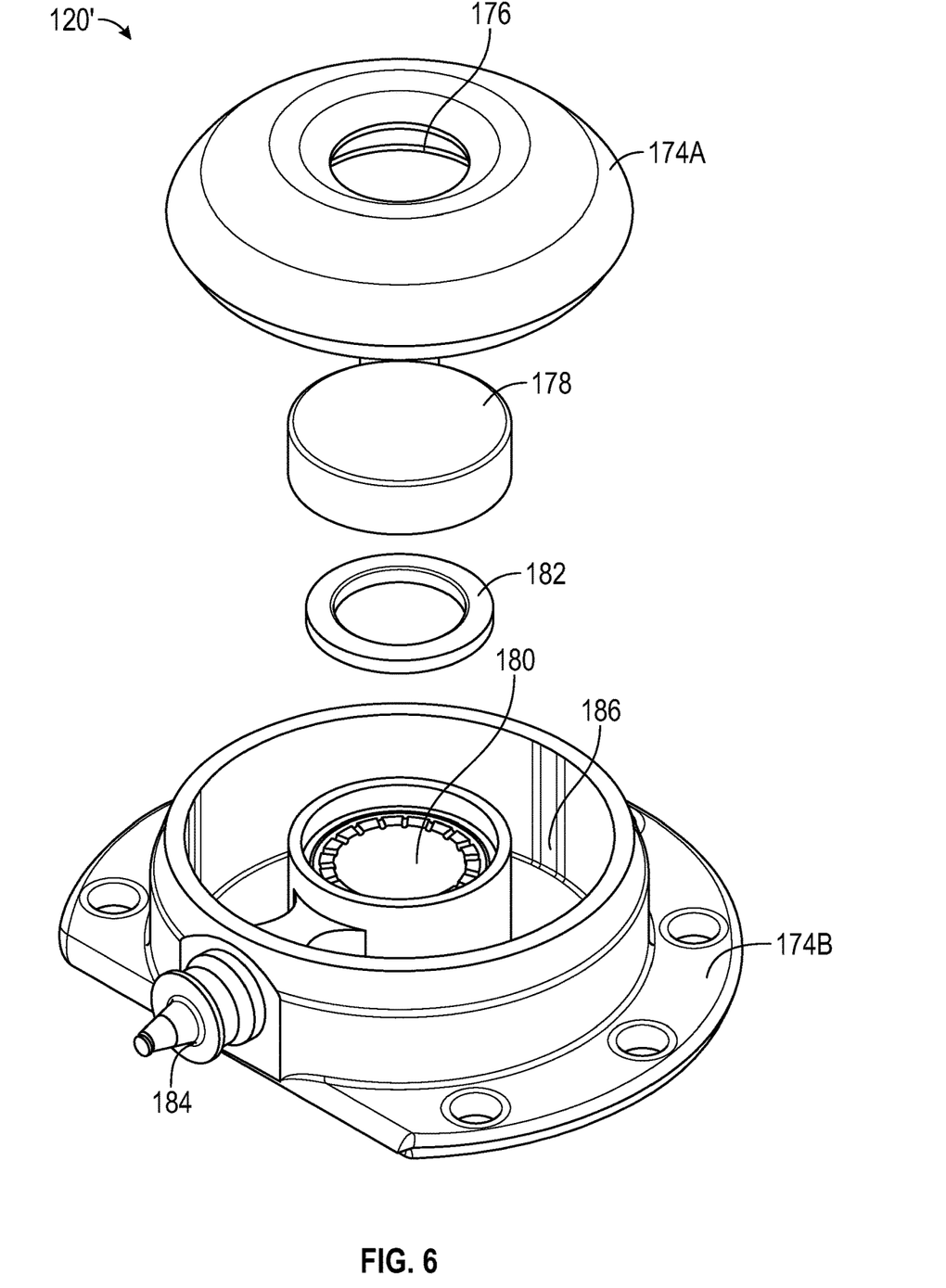
FIG. 6 is an exploded view depicting the implantable port of FIG. 5, in accordance with an embodiment of the disclosure.

FIG. 5 depicts a medical system 100" comprising an implantable device 102' in the form of an implantable port along with a manually actuated flushing pump 112 configured to enable enhanced mixing of infusate via manual barbotage, in accordance with an embodiment of the disclosure. FIG. 6 depicts an exploded view of the implantable port 102' of FIG. 5. In one embodiment, the implantable port 102' can include a housing 174, for example including a first portion 174A and a second portion 174B, which can be constructed of a material that is biocompatible and hermetically sealed, such as titanium, tantalum, stainless steel, plastic, ceramic, or the like.

In some embodiments, a first portion of the housing 174A can define an access port 176, configured to enable an introduction of an infusate into the implantable medical device 102'. The access port 176 can include a septum 178 with self-sealing properties, thereby enabling a needle or other fluid introduction mechanism to pierce the septum while maintaining a fluid impermeable seal upon removal of the needle. Fluid introduced into the access port 176 can enter an access port chamber 180. Infusate introduced into the access port chamber 180 can flow through a filter 182 and into a catheter connector 184. In some embodiments, the implantable port 102' can include electrical circuitry (such as that described in FIG. 3), configured to enable enhanced functionality and sensing. In such an embodiment, said electrical circuitry can be positioned in a compartment 186 of the implantable port 102' at least partially surrounding the access port chamber 180.

Figure 7A:
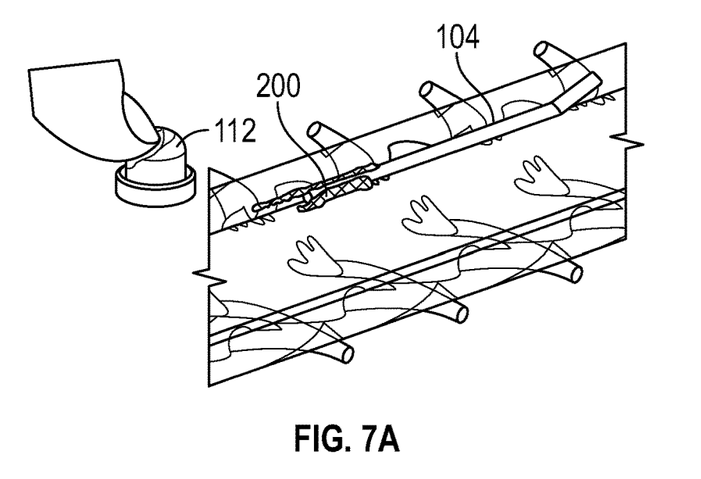
FIG. 7A depicts dispersion of medicament within cerebrospinal fluid of a patient following an initial actuation of a manually activated flushing pump, in accordance with an embodiment of the disclosure.
Figure 7B:
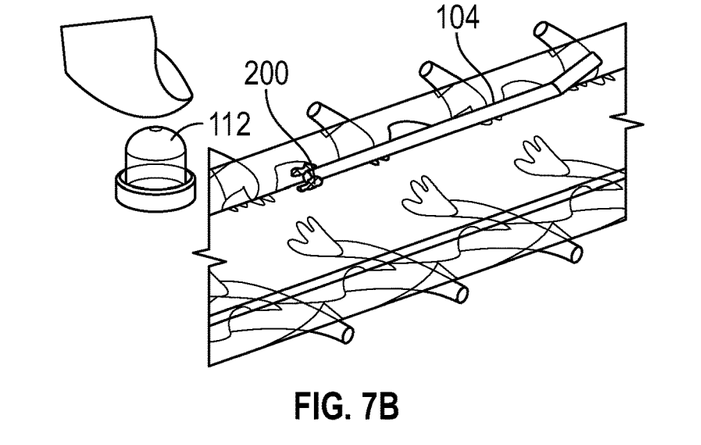
FIG. 7B depicts dispersion of medicament within cerebrospinal fluid of a patient following release of the manually activated flushing pump, in accordance with an embodiment of the disclosure.
Figure 7C:
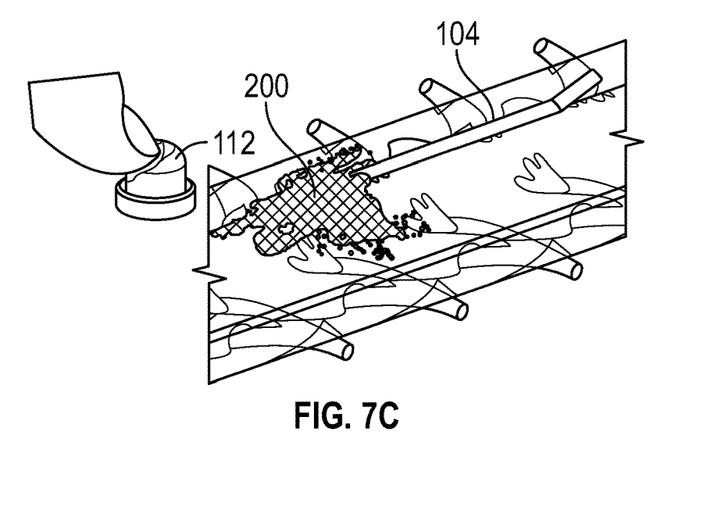
FIG. 7C depicts dispersion of medicament within cerebrospinal fluid of a patient following a subsequent actuation of a manually activated flushing pump, in accordance with an embodiment of the disclosure.

In operation, manual actuation of the flushing pump 112 enables enhanced mixing of delivered infusate. For example, with reference to FIGS. 7A-C, dispersion of medicament 200 within cerebrospinal fluid of the patient upon manual actuation of the flushing pump 112 is depicted in accordance with an embodiment of the disclosure. Following drug disbursement (e.g., via an implantable pump or port) infusate exits the catheter 104 at the targeted drug delivery site. In some cases, a combination of low circulation of the cerebrospinal fluid and relative low velocity of infusate exiting the catheter 104 can result in slow mixing of the infusate into the cerebrospinal fluid, which can adversely affect the therapeutic effect of the infusate. Accordingly, as depicted in FIG. 7A, manually depressing or actuating the flushing pump 112 can cause a rush of fluid (e.g., a combination of infusate and cerebrospinal fluid) to be expelled from the catheter 104. As depicted in FIG. 7B, subsequent release of the flushing pump 112 can cause the flushing pump to return to its original shape under a natural bias, thereby withdrawing fluid from the end of the catheter 104 into a chamber of the flushing pump 112. Thereafter, as depicted in FIG. 7C, subsequent actuation of the flushing pump 112 can cause a rush of fluid to be expelled from the catheter 104.

Accordingly, when the flushing pump 112 is pressed (e.g., through the skin of the patient) the pump 112 displaces the volume of liquid into the cerebrospinal fluid via the catheter 104. When released, the flushing pump 112 draws cerebrospinal fluid into the flushing pump 112. By repeatedly pressing the flushing pump 112, a significant mixing can be created, thereby dispersing infusate along the spinal canal. Thus, through the repeated injection and removal of fluid, the flushing pump 112 is configured to enable enhanced mixing of infusate delivered with an implantable pump or port via manual barbotage. With some medicaments, increased dispersion may significantly improve patient outcomes, particularly where the beneficial effects of the medicament are directly tied to a rapid delivery or disbursement of the medicament.

Embodiments of the present disclosure enable greater user control over spread of the medicament and dilution of the drug following infusion. The desired degree of mixing can be prescribed by a clinician based on clinical studies or perceived patient observations or effects of the medicament distribution. Moreover, embodiments of the present disclosure provide a mechanism for patient involvement, while still limiting the potential quantity of medicament delivery over longer periods of time.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An implantable infusate spread promoting system configured to enable improved dispersion of delivered infusate, the system comprising:
   an implantable device configured to enable infusate delivery to a target site within a body of a patient, wherein an implantable pump or implantable port disburses a first quantity of infusate to the target site; and
   an implantable manually actuatable flushing pump configured to remove and re-inject mixtures of bodily fluid and at least a portion of the first quantity of infusate from and to the target site with repeated pump actuation, wherein the repeated pump actuation promotes improved dispersion of the delivered infusate at the target site.

2. The implantable infusate spread promoting system of claim 1, wherein the implantable manually actuatable flushing pump is at least one of a molded rubber pushbutton, mechanical bellows, or deformable plate.

3. The implantable infusate spread promoting system of claim 1, wherein the implantable manually actuatable flushing pump comprises a chamber having a volume of between about 0.25 mL and about 2 mL.

4. The implantable infusate spread promoting system of claim 1, wherein the implantable manually actuatable flushing pump is integrally mounted within a housing of the implantable device.

5. The implantable infusate spread promoting system of claim 1, wherein the implantable manually actuatable flushing pump is fluidly coupled to a catheter extending from the implantable device.

6. The implantable infusate spread promoting system of claim 5, wherein the (Original) implantable manually actuatable flushing pump is fluidly coupled in-line with the catheter.

7. The implantable infusate spread promoting system of claim 5, wherein the implantable manually actuatable flushing pump is fluidly coupled to the catheter with a branched coupling.

8. The implantable infusate spread promoting system of claim 5, wherein the implantable manually actuatable flushing pump is configured to draw bodily fluid and infusate from an area of a patient spaced apart from a targeted drug delivery site.

9. The implantable infusate spread promoting system of claim 1, wherein the implantable manually actuatable flushing pump is actuatable through a skin of a patient.

10. The implantable infusate spread promoting system of claim 1, wherein the implantable manually actuatable flushing pump is passively actuatable through regular patient motion.

11. The implantable infusate spread promoting system of claim 1, further comprising a pressure sensor configured to detect manual actuation of the implantable manually actuatable flushing pump.

12. The implantable infusate spread promoting system of claim 11, wherein the pressure sensor is further configured to aid in detection and diagnosis of catheter occlusion, dislodgment, and kink issues.

13. The implantable infusate spread promoting system of claim 1, further comprising an external programmer in wireless communication with the implantable device.

14. The implantable infusate spread promoting system of claim 13, wherein the external programmer is configured to provide user notifications regarding actuation of the implantable manually actuatable flushing pump.

15. The implantable infusate spread promoting system of claim 1, wherein the implantable device comprises the implantable pump.

16. An implantable flushing mechanism, comprising:
an implantable pump or implantable port is configured to disburse a first quantity of infusate into a target site; and
an implantable manually actuatable flushing pump in the form of at least one of a rubber pushbutton, mechanical bellows, or deformable plate configured to remove and re-inject mixtures of bodily fluid and at least a portion of the first quantity of infusate from and to the target site within a body of a patient with repeated pump actuation, wherein the repeated pump actuation promotes improved dispersion of infusate delivered by an implantable infusion pump.

17. The implantable flushing mechanism of claim 16, wherein the implantable manually actuatable flushing pump comprises a chamber having a volume of between about 0.25 mL and about 2 mL.

18. The implantable flushing mechanism of claim 16, wherein the implantable manually actuatable flushing pump is fluidly coupled to a catheter extending from the implantable device.

19. The implantable flushing mechanism of claim 16, wherein the implantable manually actuatable flushing pump is actuatable through a skin of a patient.

20. An implantable infusate spread promoting system, comprising:
an implantable pump configured to enable infusate delivery of a first quantity to a catheter positioned within a body of a patient and to a target site; and
an implantable manually actuatable flushing pump configured to remove and re-inject quantities of fluid of between about 0.25 mL and about 2 mL with repeated pump actuation, wherein each quantity of fluid comprises a mixture of bodily fluid and at least a portion of the first quantity of infusate, and the repeated pump actuation promotes improved dispersion of the delivered infusate, the implantable manually actuatable flushing pump fluidly coupled to the catheter of the implantable pump.

21. The implantable infusate spread promoting system of claim 1, wherein the implantable device comprises the implantable port.

* * * * *